United States Patent [19]
Sires

[11] Patent Number: 5,112,354
[45] Date of Patent: May 12, 1992

[54] BONE ALLOGRAFT MATERIAL AND METHOD

[75] Inventor: Bryan S. Sires, Seattle, Wash.

[73] Assignee: Northwestern University, Evanston, Ill.

[21] Appl. No.: 437,189

[22] Filed: Nov. 16, 1989

[51] Int. Cl.$^5$ .............................................. A61F 2/28
[52] U.S. Cl. .............................................. 623/16
[58] Field of Search .................. 623/16, 66; 424/549

[56] References Cited

U.S. PATENT DOCUMENTS

| | | | |
|---|---|---|---|
| 4,277,238 | 7/1981 | Katagiri | 623/16 X |
| 4,627,853 | 12/1986 | Campbell et al. | 623/16 |
| 4,932,973 | 6/1990 | Gendler | 623/16 |
| 4,946,792 | 8/1990 | O'Leary | 623/16 X |

OTHER PUBLICATIONS

Knapp et al, Use of Cortical Cancellous Allograft etc., Clin. Orthop., vol. 229, p. 98 (1988).
Glowacki et al, Application of the Biological Principle etc., Lancet, vol. 2, p. 959 (1981).
Gendler, Perforated Demineralized Bone Matrix: A New Form etc., J. of Biomed. Mat. Res., vol. 20, p. 687 (1986).
Mulliken et al, Induced Osteogenesis—The Biological Principle etc., J. of Surg. Res., vol. 37, p. 487 (1984).
Urist, Surface Decalcified Allogenic Bone Implants etc., Clin. Orthop., vol. 546, p. 37 (1968).

*Primary Examiner*—David J. Isabella
*Attorney, Agent, or Firm*—Tilton, Fallon, Lungmus

[57] ABSTRACT

A textured, demineralized, and unitary mammalian bone section for providing a rigid, foraminous, collagen scaffold for allogenic skeletal reconstruction. The allograft is prepared by treating a section of cadaver bone to remove all soft tissue, then texturing the bone surface to produce a pattern of holes of selected size, density, and depth, and finally demineralizing the bone section to leave a rigid, insoluble collagen scaffold suitable for osteoinduction upon implantation. All such steps are performed with minimal denaturing of the extracellular matrix proteins which remain bound to the collagen scaffold and which are necessary to complete the process of new bone formation.

12 Claims, 1 Drawing Sheet

BONE ALLOGRAFT MATERIAL AND METHOD

BACKGROUND AND SUMMARY

Reconstructive bone surgery techniques commonly utilize two sources of material for repairing bone defects caused by congenital anomaly, disease, or trauma. They are autologous bone grafts harvested from the same patients in which they are then implanted, and foreign material (alloplastic) grafts. Both are used to fill voids left by the removed defects, and both have significant problems associated with their use.

Autologous bone grafts are usually harvested from the calvarium, ribs, ilicac crests, and tibia. The harvest time and morbidity associated with such donor sites is often greater than that for the primary reconstruction. In addition, autologous grafts are limited in their size and shape, the quantity of bone obtainable, and often have unpredictable resorption rates.

Alloplastic materials used for bone reconstruction include silicone, methylmethacrylate, ceramic (hydroxyapatite), polytetrafluoroethylene, and titanium. Complications associated with the use of such graft materials include foreign body reactions, extrusion, and infection. The fact that a wide variety of such materials have been used in the past and are used currently indicates that no single material has been found that is superior to the others and that overcomes the aforementioned problems.

In recent years, attention has focused on experimental work in the field of allogenic demineralized bone grafts, that is, demineralized bone graft materials taken from a cadaver of the same species as the patient. Such grafts have shown a unique ability to induce undifferentiated mesenchymal cells to form cells that are part of the endochondral bone formation cascade. The transformed cell types include chondroblasts and osteoblasts and they appear in a characteristic time sequence. Application in several animal models have successfully demonstrated that demineralized bone heals by the mechanism of osteoinduction rather than osteoconduction or "creeping substitution" found in conventional grafts. (Mulliken et al, Induced Osteogenesis—The Biological Principle and Clinical Applications, J. of Surg. Res., Vol. 37, p. 487, 1984). This implies a transformation of an undifferentiated cell into one with a specific function as opposed to the migration of an already differentiated cell type into the area of interest.

Clinically, decalcified autogenous implants have been successfully used on a small scale for spinal fusions and surface-demineralized allogenic cortical bone for inter-transverse process fusions. (Urist, Surface Decalcified Allogenic Bone Implants—A Preliminary Report of Ten Cases and Twenty Five Comparable Operations with Undecalcified Lyophilized Bone Implants, Clin. Orthop., Vol. 546, p. 37, 1968; Knapp et al, Use of Cordical Cancellous Allograft for Posterior Spinal Fusion, Clin. Orthop., Vol. 229, p. 98, 1988). It has also been shown that the volume of bone induced by the demineralized grafts is proportional to the external surface area of the implanted matrix. (Glowacki et al, Application of the Biological Principle of Induced Osteogenesis for Craniofacial Defects, Lancet, Vol. 2, p. 959, 1981). This is of importance because it means that it is possible to fill a bony defect of known dimensions with the end result being living integrated bone.

Since demineralization requires intimate exposure of bone matrix to the demineralizing agent (dilute hydrochloric acid), only very small sections of intact cadaver bone have been successfully used for reconstruction. More commonly, the cadaver bone (from an allogenic source, although material from xenogenic sources has been used experimentally) is pulverized into tiny particles of specific size so that bone material may be thoroughly contacted by the demineralizing agent. The treated particles are then washed, heated, and finally combined with water to form a paste that has been referred to as demineralized bone matrix (DBM). Under ideal conditions, when the DBM paste is surgically implanted within the body to repair a bony defect, it transforms mesenchymal stem cells into chondroblasts that form cartilage and, over a period of a few months, evolve into solid bone which is capable of remodelling. Until such transition has occurred, however, the area of restorative treatment provides no appreciable structural strength.

Accordingly, a main aspect of this invention lies in providing a rigid graft material that may be dimensioned to replace a section of a patient's bone and that will retain its structural integrity from the time of implantation and throughout the period of osteoinduction and assimilation. It is also an aspect of this invention to provide a method for treating cadaver bone so that rigid allograft sections of any desired size may be obtained and used for implantation. It is a specific object of the invention to provide a method for demineralizing cadaver bone segments of any required size, including relatively large sections, and of enhancing the osteoinductive potential of such allografts.

Briefly stated, demineralization treatment and osteoinductive potential are enhanced by mechanically texturing the grafts with a reproducible geometric pattern of holes or pores, thereby increasing the surfaces exposed to the demineralizing agent and subsequently exposed for interaction with the mesenchymal cells. The transversely-extending holes should have diameters within the general range of 200 to 2000 um, preferably 500 to 800 um, and the spacing between adjacent holes should fall within the general range of 100 to 1200 um, preferably 300 to 700 um. The depth of the holes may vary, it being unnecessary for all of the holes or pores to pass completely through the bone section. The preferred partial distance is believed to be about 30 to 50% of the bone thickness, the general range being 5 to 90%.

In the method for preparing the bone allograft, a section of mammalian cadaver bone is first treated to remove all soft tissue, including marrow and blood, and is then textured, preferably by laser, to form a multiplicity of holes of selected size, spacing, and depth. The textured bone section is then immersed and demineralized, preferably in a dilute acid bath (e.g., 0.6 M HCl), and is further treated in a defatting solution to remove remaining marrow and intra-matrix cells. Any remaining cell debris and cell surface antigens are removed during that final step and, by the same process, the graft is also sterilized without at the same process, the graft is also sterilized without at the same time destroying its biological (osteoinductive)activity. Such activity is retained because of the biologically-active extracellular matrix proteins that remain bound to the rigid collagen scaffold of the graft. Following the texturing and chemical steps, the grafts may be freeze-dried and stored in sterile bags at conventional room temperature for periods of up to one year and perhaps longer prior to allogenic implantation.

Other features, advantages, and objects of the invention will become apparent from the specification and drawings.

DRAWINGS

DETAILED DESCRIPTION OF PREFERRED EMBODIMENT

Figure 1:
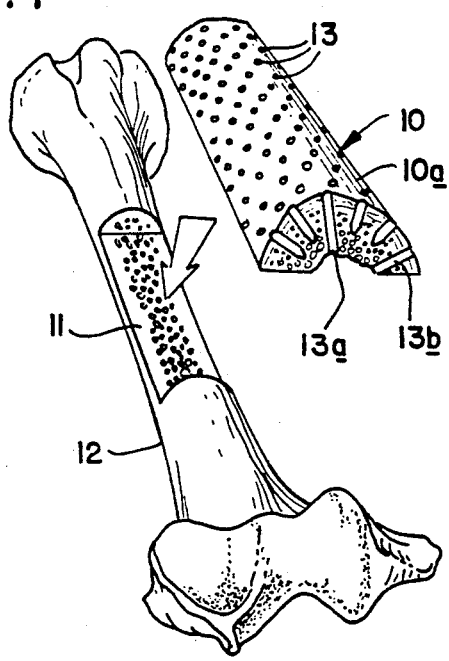
FIG. 1 is a perspective view illustrating the prepared site for a bone graft and a textured and demineralized allograft embodying the invention for implantation at that site.

Referring to the drawings, the numeral 10 generally designates an allograft in the form of a textured, demineralized section of cadaver bone dimensioned for implantation in the space or cavity 11 surgically formed in a bone 12 of a patient. For clarity of illustration, all extraneous tissue is omitted from the views of FIGS. 1 and 2. While the allograft shown in the drawings is generally semi-cylindrical and is dimensioned to be received in a space of similar shape excised in a long bone (humerus), it is to be understood that other implantation sites may be involved and that the size and shape of the allograft will vary accordingly. Both endochondral long bone and lamellar bone can be used as a source of material. It is not necessary that the allograft 10 be taken from a cadaver bone that corresponds with the patient's bone to be restored although it is apparent that where the allograft is a large one, constituting a major or at least significant portion of a large bone such as the femur, tibia, or humerus, a large cadaver bone must also be used as the source. Attachment means in the form of surgical pins or cements may be used for temporarily securing the allograft in place (until osteogenesis has occurred and the patient's bone is fully reformed) although such attachment means may be unnecessary if the graft and site are configured so that a tight, frictional (and preferably interlocking) fit is provided.

Figure 2:
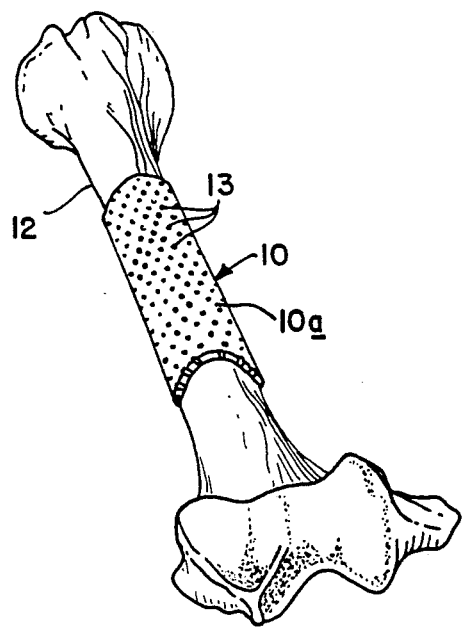
FIG. 2 is a perspective view similar to FIG. 1 but showing the allograft in place.

Allograft 10 consists of a collagen matrix or scaffold to which biologically-active extracellular matrix proteins remain bound. All soft tissue, including marrow, fat, and blood, have been removed. Minerals, particularly hydroxyapatite, have also been extracted. In addition, a multiplicity of pores or holes 13 extend into the allograft or bone section 11 from the outer surface 10a thereof. As shown in FIG. 1, the pores extend generally perpendicular to the outer surface of the graft so that, in the illustration given, such pores project radially inwardly. The size, density, and depth of the pores is selected to maximize the surface area of the implant while minimizing the loss of structural integrity.

Figure 3:
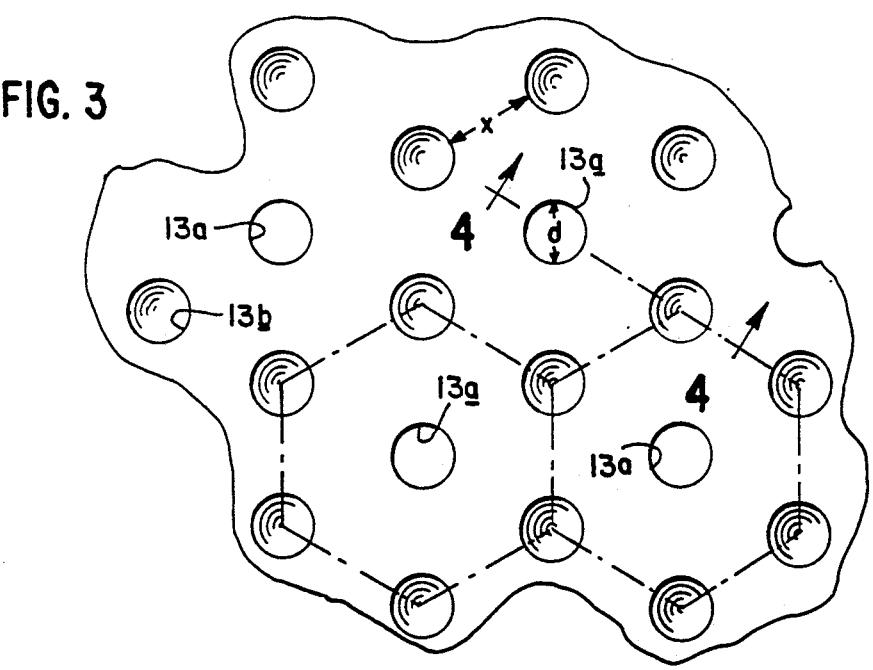
FIG. 3 is a greatly enlarged fragmentary plan view depicting the pattern of pores or openings formed in an allograft embodying this invention.

FIG. 3 reveals that the pores are arranged in a geometric pattern with some pores 13a extending completely through the collagen scaffold and pores 13b extending only partially through that scaffold. A particularly effective pattern is believed to be a repeating hexagonal arrangement with through-pores 13a being located at the centers of the hexagons and the partial-depth pores being located at the apices of such arrangements. The pores may be mechanically drilled, although a preferred method is by means of a laser. An Erbium YSGG laser is suitable because of its capability of cutting bone with minimal damage, particularly minimal thermal damage, to the collagen matrix and to the proteinaceous growth factor bound to that matrix. Effective results have been achieved with a laser having maximum power of 10 Watts, maximum energy per pulse of 1 Joule, and a pulse repetition rate of 10 pulses per second. At a selected pulse energy of 57 mJ per pulse, a bone cutting rate of 40 um per pulse may be achieved. To produce a pore having a depth of 2.5 millimeters (2500 um) therefore requires 62 to 63 pulses and a cutting interval of 6.2 to 6.3 seconds. As examples of specific laser settings that may be used, V=1400 volts, f=1 Hz, A=275 mJ, and fluence=35J per cm$^2$. While an Erbium YSGG laser is particularly effective, other types of lasers, such as an Erbium YAG laser, may instead be used.

Any suitable means may be provided for indexing movement of either the bone or the laser so that a selected pattern of closely-spaced pores is produced. The laser should be adjusted and operated so that the diameter of each pore falls within the general range of 200 to 2000 um, preferably 500 to 800 um, with the edges of adjacent pores spaced apart distances falling within the general range of 100 to 1200 um, preferably 300 to 700 um. The preferred spacing corresponds with the optimal particle size range previously noted by Reddi & Huggins (J. Biomed. Mat. Res., Vol. 19, p. 233, 1985) for inducing the osteoinductive process, apparently because it optimizes the surface area to volume ratio of the particles from which a DBM paste may be formed. The surface areas for attachment of the mesenchymal cells must be larger than the cells themselves if effective anchoring and osteogenesis is to occur.

With respect to pore diameter, 200 um is believed to be a practical lower limit because pores smaller than that cannot readily be formed with a laser. Pores of 500 um or larger in diameter are preferred because of the relatively smaller sizes of the mesenchymal cells. While pores of larger diameter increase the exposed surface area and therefore promote osteogenic ingrowth, pores larger than 2000 um should not be created because of adverse effects on the structural integrity of the bone section.

Figure 4:
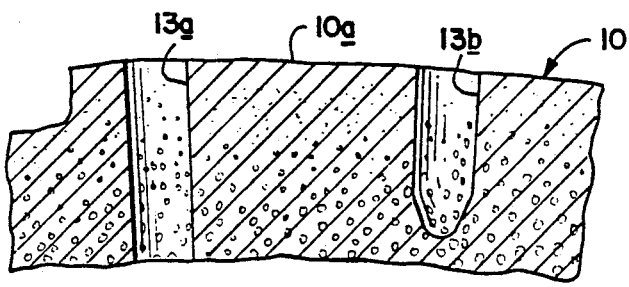
FIG. 4 is a still further enlarged fragmentary sectional view taken along line 4—4 of FIG. 3.

Pore depth may be varied depending largely on the shape of the bone graft section and the directions in which the pores extend. For example, in the embodiment illustrated, the longitudinal axes of the pores are perpendicular to the semi-cylindrical outer surface of the graft and, therefore, the radially-extending pores have their axes converging inwardly. If the pore density at the inner and outer surfaces of the bone are to be approximately the same, then it is apparent that a substantial proportion of the pores must extend only partially into the bone from its outer surface. The extent of penetration may range from 5 to 90% of the bone thickness depending in part on the size of the graft and its radius of curvature. On the other hand, where a bone graft section has a relatively flat outer surface, a greater proportion of the pores may extend completely through the graft. Although in such a case the pore density may have to be decreased to maintain structural integrity. Thus, if the configuration of the graft section is such that the axes of the pores extend along parallel lines, all or substantially all of the pores may extend completely through the graft section.

Where the pores are formed by a laser, those that extend only partially through the thickness of a bone are tapered or generally conical at their distal ends. In the schematic view of FIG. 4, it will be observed that pore 13b which extends only partially through the graft is generally conical at its closed end whereas pore 13a that extends completely through the graft is substantially cylindrical. It is to be understood that the term "pore diameter" as used herein refers to the diameter of a pore at the outer surface 10a of the graft.

The use of a laser to form pores in the graft is highly desirable because it reduces complexities and allows greater speed for the texturing operation, but such advantages would be of no value if laser treatment resulted in damage to the chemical structure of the collagen scaffold, including denaturing of the extracellular matrix proteins. The further discovery that a laser may be effectively used without appreciably damaging the collagen or denaturing the extracellular matrix proteins is therefore believed highly significant. Inspection of textured grafts under polarized light (where normal collagen appears orange and damaged collagen black) reveals only slight differences between a laser-textured bone and one textured by mechanical drilling, and such differences become indistinguishable and insignificant when the grafts are later subjected to demineralization. For the same reasons, it has been found that cooling of a bone section, for example, to minus 180° C. by the use of liquid nitrogen, prior to and during the laser texturing process is unnecessary; such texturing may be carried out at room temperature (e.g. 22° C.) with no significant damage to the collagen and extracellular matrix proteins.

Since texturing or pore formation is carried out prior to demineralization, such texturing plays important roles both in achieving completeness of demineralization and later in promoting osteoinduction because of the increased surface area which allows a greater number of biologically-active proteins bonded to the collagen scaffold to interact with mesenchymal cells for potentiation of the osteoinductive process.

A first step in the treatment of a harvested cadaver bone section is the removal of marrow and the deblooding of the section. Marrow removal is achieved by scraping or coring, and deblooding is obtained by placing the bone section in a suitable solution that will not enzymatically denature the exposed proteins. A sodium chloride solution of 0.15 M with 50 mM Tris, along with protease inhibitors, using sterile distilled water (pH 7.4) at a temperature of 4° C., has been found effective, but variations in the formulation might be made as well known to those in this field. With regard to the protease inhibitors, one combination that has been found particularly effective is as follows:

Phenylmethylsulfonyl fluoride (1 mM) in isopropyl alcohol
Benzamidine (5 mM)
N-ethylmaleimide (1 mM) in ethanol
E-amino-n-caproic acid (10 mM)

Continuous stirring of the treatment bath is recommended for an interval of at least 2 hours with all red-tinged fluid being aspirated off and replace with fresh solution. The treatment step is repeated as many times as necessary to eliminate the blood-tinged color. The treated bone section is then dried and frozen at −20° C. pending the texturing and demineralizing steps.

Texturing is carried out as already described, preferably by means of a laser, to provide an arrangement of pores of specified size, density, and depth. Following such texturing, the bone section is demineralized, preferably by placing it into a dilute acid bath (e.g., 0.6 M HCl) which also contains a suitable protease inhibitor. Where the demineralizing agent is dilute acid, the protease inhibitor should be pepstatin (1 ug/ml) because it is the only such inhibitor that is active at acidic pH. Although a dilute acid demineralizing agent is preferred, it has been noted that demineralization may be carried out using ethylene diamine tetracetic acid (EDTA) (0.5 M) containing protease inhibitors such as those indicated above for the sodium chloride rinses. (Kuboci et al, J. Dent. Res., Vol. 58, p. 1926, 1979).

A solution/bone ratio of 1.0 grams of bone per 20 milliliters of 0.6 M HCl solution has been found suitable with treatment being carried out at 4° C. for a variable period of time with stirring, depending on bone thickness. Complete demineralization may be important and may be determined by radiographic inspection since any remaining mineral content will appear radiopaque; however, small amounts of mineralization may be acceptable and may even be beneficial because of increased structural integrity. Following demineralization, the bone section is rinsed in sterile water several times.

Thereafter, the demineralized and textured bone grafts are placed in a bath of a defatting solvent to remove all remaining cell debris and cell surface antigens. A defatting solution of chloroform and methanol in a 1:1 concentration has been found effective, but other suitable solvents may be used. A ratio of 1.0 grams of bone per 10 milliliters of defatting solution is recommended with the bath kept at 4° C. with stirring for an interval of approximately 2 hours. The step may be repeated two or more times until complete defatting has taken place, at which time the treated bone section should be rinsed in sterile distilled water.

It has been found that the final chemical step of defatting the bone graft also functions as a particularly effective way of sterilizing the graft and retaining more biological activity when compared to other methods of sterilization. (Prolo et al, Clin. Orthop. Vol. 168, p. 230, 1982) Following such treatment, the graft may be freeze-dried and packaged in a sterile wrapper. The result is an acellular, demineralized, defatted, dried bone graft having a reproducible, geometric arrangement of pores extending inwardly from its surface and functioning to optimize the surface area of the graft and enhance its osteoinductive capabilities. Microscopically, one sees a collagen scaffold for structural support with exposed extracellular matrix proteins attached. Such proteins, along with other circulating factors, direct the osteoinductive process to completion. The shelf life for such a sterile, freeze-dried bone graft is believed to be at least one year at room temperature.

While in the foregoing I have disclosed an embodiment of the invention in considerable detail for purposes of illustration, it will be understood by those skilled in the art that many of these details may be varied without departing from the spirit and scope of the invention.

I claim:

1. A method for preparing a bone allograft comprising the steps of treating a section of cadaver bone to remove all soft tissue therefrom; then texturing said section b forming a multiplicity of holes extending inwardly from a surface thereof; said holes being of a diameter within the range of 200 to 2000 um and being spaced apart distances within the range of 100 to 1200 um; and then demineralizing said section by immersing the same in a demineralizing bath containing a protease inhibitor for retaining the bioactivity of the extracellular matrix proteins bound thereto and providing a rigid collagen scaffold for reconstructive allogenic implantation in a living subject.

2. The method of claim 1 in which said section is demineralized by immersing the same in a dilute acid bath.

3. The method of claims 1 or 2 in which said holes are of a diameter within the preferred range of 500 to 800 um.

4. The method of claims 1 or 2 in which said holes are spaced apart distances within the preferred range of 300 to 700 um.

5. The method of claims 1 or 2 in which some of said holes extend completely through said section and others of said holes extend only partially through said section.

6. The method of claim 5 in which said others of said holes extend 5 to 90% of the thickness of said section.

7. The method of claim 6 in which said others of said holes extend 30 to 50% of the thickness of said section.

8. The method of claims 1 or 2 in which said holes are formed in said section by a laser beam.

9. The method of claims 1 or 2 in which said holes have their longitudinal axes perpendicular to said surface.

10. The method of claim 9 in which said surface is curved and said axes are generally converging in directions extending inwardly from said surface.

11. The method of claim 10 in which some of said holes extend completely through said section and others of said holes extend only partially through said section.

12. The method of claims 1 or 2 in which there is the further step of defatting and sterilizing said section in a liquid medium that dissolves fat without denaturing extracellular matrix proteins.

* * * * *

UNITED STATES PATENT AND TRADEMARK OFFICE
CERTIFICATE OF CORRECTION

PATENT NO. : 5,112,354
DATED : May 12, 1992
INVENTOR(S) : Bryan S. Sires It is certified that error appears in the above-identified patent and that said Letters Patent is hereby corrected as shown below:

```
On the coversheet, the following coinventors
should be identified:

Mark L. Zukowski, Chicago, Illinois
    Joseph T. Walsh, Evanston, Illinois
```

Signed and Sealed this

Thirty-first Day of August, 1993

*Attest:*

BRUCE LEHMAN

*Attesting Officer*   *Commissioner of Patents and Trademarks*